US00PP11590P

United States Patent [19]

Jonkers

[11] Patent Number: Plant 11,590

[45] Date of Patent: Oct. 24, 2000

[54] IMPATIENS PLANT NAMED 'DIDI ORARE'

[75] Inventor: J. B. (Hanneke) Jonkers, Hoorn, Netherlands

[73] Assignee: Goldsmith Plants, Inc., Gilroy, Calif.

[21] Appl. No.: 09/078,638

[22] Filed: May 14, 1998

[51] Int. Cl.[7] ..... A01H 5/00

[52] U.S. Cl. ..... Plt./317

[58] Field of Search ..... Plt./317

[56] References Cited

U.S. PATENT DOCUMENTS

P.P. 3,918 6/1976 Hope et al. ..... Plt./317

P.P. 10,256 2/1998 Cosner et al. ..... Plt./317

OTHER PUBLICATIONS

GTITM UPOVROM Citation for 'Didi Orange' as per QZ PBR 971002; Sep. 16, 1997.

*Primary Examiner*—Howard J. Locker
*Assistant Examiner*—Kent L. Bell
*Attorney, Agent, or Firm*—Rothwell, Figg, Ernst & Manbeck

[57] ABSTRACT

A new and distinct cultivar of Impatiens plant, and named 'Didi Orare' is provided. 'Didi Orare' is distinct in its orange colored fully double flowers, its early and free flowering, and its basal branched, compact growth habit.

3 Drawing Sheets

BACKGROUND OF THE NEW PLANT

The present invention comprises a new and distinct cultivar of impatiens, botanically known as *Impatiens walleriana*, and hereinafter referred to by the cultivar name 'Didi Orare', and is characterized by the following combinations of repeatedly observed traits:

1. Fully double flowers,
2. early flowering,
3. compact basal branching, and
4. free flowering.

Asexual reproduction of this cultivar by stem cuttings taken during November, 1996, at Andijk, The Netherlands, has demonstrated that the characteristics of the new cultivar as herein described are firmly fixed and are retained through successive generations of such asexual propagation, such reproduction establishing that the plant does in fact maintain the characteristics described in successive generations. The female parent (i.e., the seed parent) was an *Impatiens walleriana* named IN-1792-7 (unpatented) and the male parent (i.e., pollen parent) was an *Impatiens walleriana* named IM-795-3 (unpatented). The cross was made in 1995 and the seedling was selected in 1996.

This new cultivar has been identified as Impatiens 'Didi Orare'. The new cultivar is being marketed under the trademark name Double Diamond Orange.

DESCRIPTION OF THE PHOTOGRAPHS

This new impatiens plant is illustrated by the accompanying photographic drawings in full color, the colors shown being as true as can be reasonably obtained by conventional photographic procedures.

DESCRIPTION OF THE NEW CULTIVAR

Figure 1:
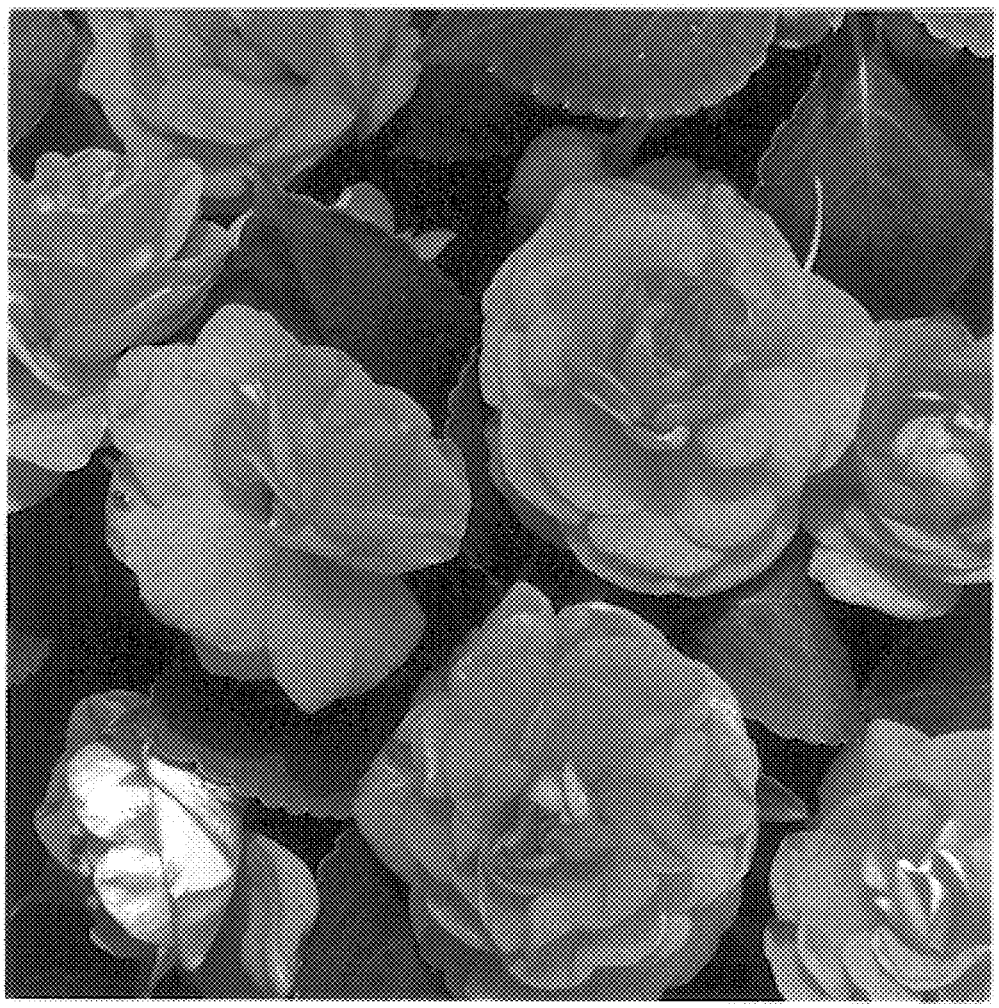
FIG. 1 shows the buds, flowers, and foliage.
Figure 2:
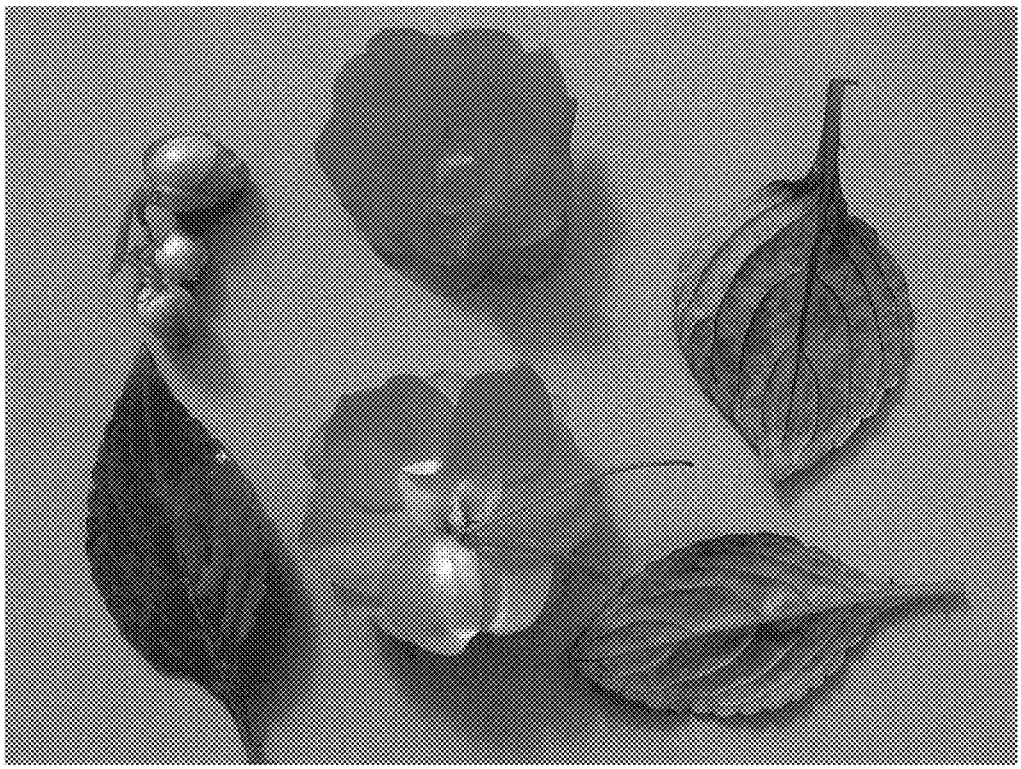
FIG. 2 shows buds and the upper and lower sides of flower and foliage.
Figure 3:
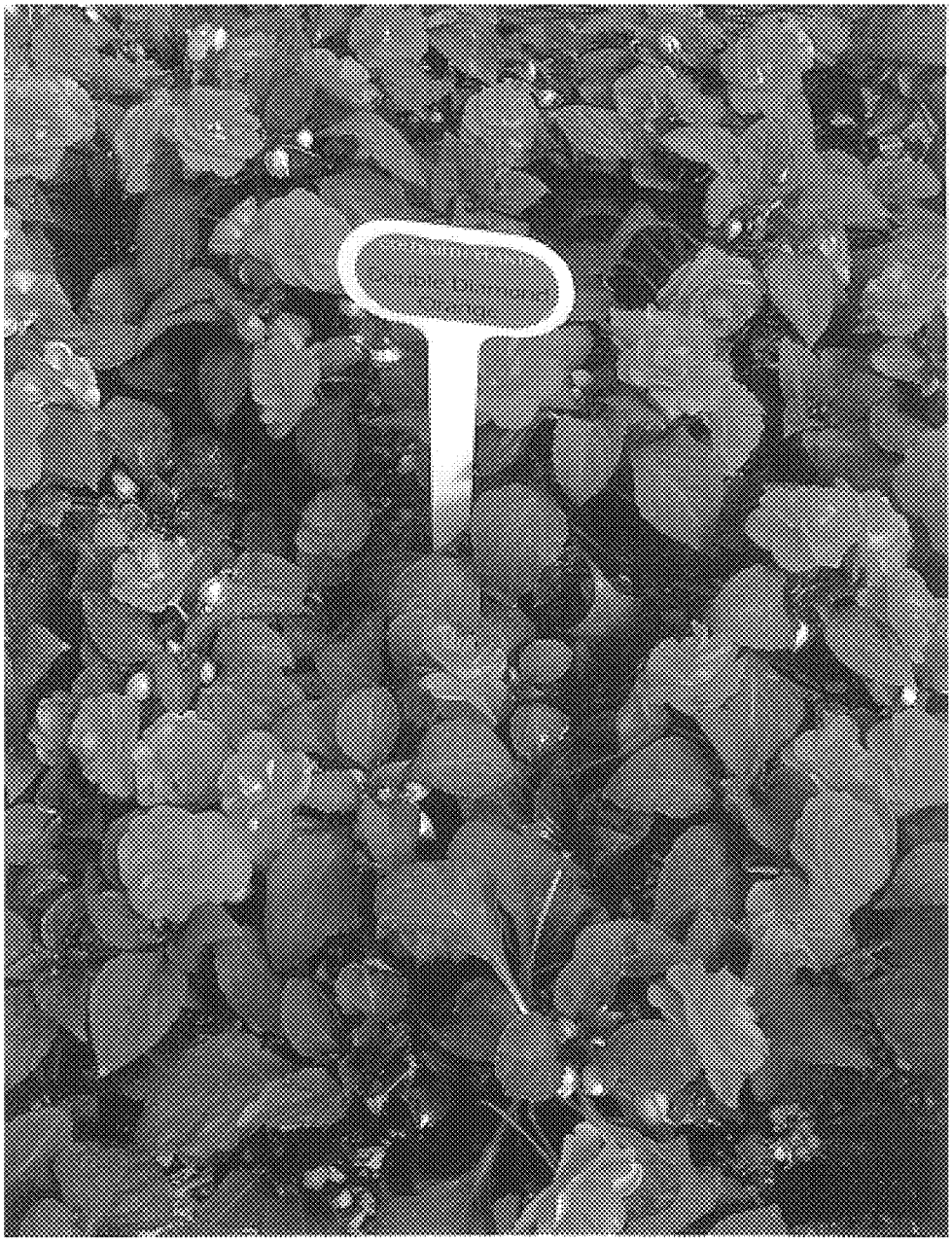
FIG. 3 shows a top perspective view of typical plants of the new cultivar.

The following observations and measurements describe plants grown outside in the field in Andijk, The Netherlands.

Measurements were recorded in August, 1997, on plants approximately 14 weeks old. Fully developed organs were used for measurements and color descriptions, unless otherwise indicated. Color references are made to the R.H.S. Colour Chart of The Royal Horticultural Society, London, England, except where general color terms of ordinary significance are used.

'Didi Orare' has not been observed under all possible environmental conditions. The phenotype may vary with variations in environment and horticultural practices, such as temperature, light intensity, day length, fertilization and propagation procedure, without any change in genotype.

Parentage:

*Female parent.*—*Impatiens walleriana* IN-1792-7 (unpatented).

*Male parent.*—*Impatiens walleriana* IM-795-3 (unpatented).

Propagation:

*Type cutting.*—Stem (internodal) cutting with two nodes and attached leaves.

*Time to initiate roots.*—10–14 at 70–75 degrees F with a fully developed root mass at 21 days.

*Rooting habit.*—Fibrous, branching, adventitious root system.

Plant description:

*Form.*—Upright

*Growth habit.*—Upright branching plant habit with upper leaves and flowers produced in whorls. When grown in a 4 inch pot for 10–12 weeks the height is approximately 4–5 inches and the width is approximately 5 inches.

*Foliage Description.*—Leaves are simple. Lower leaf arrangement is alternate with upper leaves arranged in whorls of 5. Leaf shape is ovate with acute apex and acute base. Leaf size is 4.5 cm×3 cm. Leaf margin is crenate with ciliation. Leaf surface is glabrous. Leaf color is green. The upper surface is yellow-green group 147A. Under surface is yellow-green group 147B with purple mottling ranging from 182A to 182C through 183D. Venation is pinnate 147A for the upper surface and 147B for the lower surface.

*Petiole*.—Petiole length is 2 cm; and diameter is 0.2 cm; Color is 183A.

Flower description:

*Flowering Habit*.—Rooted cutting to full flowering plant in seven weeks. Indeterminate, flowering continuously. Flowers develop in the upper leaf axils.

*Natural flowering season*.—Flowers continuously throughout the year.

*Flowers borne*.—On pedicels which are yellow-green 145A and 3 cm long in clusters of 2–7 flowers with a peduncle color of yellow-green 145A and length of 2 cm long.

*Spur*.—Short spurred; length is 3.5 cm; color is 145C with reddish tinge towards the apex.

*Quantity of flowers*.—Floriferous. Each axillary cluster of 2–7 flowers developing progressively from the leaf whorls so that buds as well as mature flowers are visible at the same time in large numbers.

*Petals*.—Number of petals 20–25, with all petals overlapping. Outer petals average 2.2 cm length×2.0 cm width and inner petals average 1.0 cm length ×0.7 cm width All petals are slightly cupped.

*Flower color*.—Upper surface: Red group 40A; occasionally small white 155B petals in the center of the flower will appear. Their presence or absence is affected by growing conditions and use of growth regulators. Lower surface: Red group 41B, occasionally some petals will have white 155D markings or fading of color on the under side of the petals due to light deficiency from crowded petals.

*Flower size*.—Approximately 4 cm wide and 4 cm long.

*Nectary length*.—Approximately 2 cm long.

*Reproductive organs*.—No reproductive organs.

Disease and Insect Resistance

No known susceptibility to diseases or insects noted to date.

Comparison with the Known Cultivars

When 'Didi Orare' is compared to Impatiens 'Fiesta Tropical Orange', (unpatented) it is found that 'Didi Orare' exhibits a more vigorous plant habit and is also more floriferous.

When 'Didi Orare' is compared to 'IN1792-7' and 'IM-795-3', the parental cultivars, the instant cultivar has double flowers and the parental cultivars are both single flowering.

I claim:

1. A new and distint cultivar of Impatiens plant named 'Didi Orare', substantially as described and illustrated herein, characterized particularly as to novelty by its fully double orange colored flowers, its early and free flowering, and its basal branched, compact growth habit.

* * * * *